United States Patent [19]

Hoehn et al.

[11] 4,256,588

[45] Mar. 17, 1981

[54] SEPARATION AND RECOVERY OF B AND T LYMPHOCYTES

[75] Inventors: Harvey H. Hoehn, Hockessin; Stephen T. Toy, Wilmington, both of Del.

[73] Assignee: E. I. Du Pont de Nemours and Company, Wilmington, Del.

[21] Appl. No.: 90,677

[22] Filed: Nov. 2, 1979

[51] Int. Cl.$^3$ .............................................. B01D 15/00
[52] U.S. Cl. ..................................... 210/692; 210/927
[58] Field of Search ............... 128/214 R; 210/24, 40, 210/DIG. 23

[56] References Cited

U.S. PATENT DOCUMENTS

| | | | |
|---|---|---|---|
| 2,682,268 | 6/1954 | Ryan et al. | 210/DIG. 23 |
| 3,448,041 | 6/1969 | Swank | 210/DIG. 23 |
| 3,929,130 | 12/1975 | Hargest | 210/DIG. 23 |
| 4,050,451 | 9/1977 | Columbus | 128/2 F |
| 4,064,042 | 12/1977 | Kunin | 210/DIG. 23 |

OTHER PUBLICATIONS

Trizio et al., "Separation of T and B Lymphocytes by Nylon Wool Columns: Evaluation of Efficacy by Functional Assays in Vivo", The Jouranl of Immunology, vol, 113, No. 4, Oct. 1974, pp. 1093–1097.

Rabinowitz, Y. "Separation of Lymphocytes, Polymorphonuclear Leukocytes and Monocytes on Glass Columns, Including Tissue Culture Observations", Blood, vol. 23, No. 6 (Jun.), 1964, pp. 811–828.

Eisen et al., "Isolation of Pure Human Peripheral Blood T-Lymphocytes", Immunological Communications, 1(6), 1922, pp. 571–577.

Primary Examiner—Ivars C. Cintins

[57] ABSTRACT

A process for the separation of B and T lymphocytes comprising passing a suspension of a mixture over a bed of synthetic polymer granules whereby the B leukocytes adhere to the granules and the T lymphocytes pass through the bed.

7 Claims, No Drawings

SEPARATION AND RECOVERY OF B AND T LYMPHOCYTES

BACKGROUND OF THE INVENTION

1. Field of the Invention

The present invention relates to the use of granulated resins such as polyamide for the separation of B lymphocytes and T lymphocytes in suspension, e.g., in blood. The desirability of being able to separate these lymphocytes and to administer T lymphocytes to patients has become of increasing importance in recent years with the advent of chemotherapy of cancer and organ transplants.

2. State of the Prior Art

Polyamide fibers have been used in the past to separate white cells such as granulocytes from blood as well as to separate T lymphocytes from suspensions of lymphocytes. The recovery of cells from packs of fibers is undesirably low.

SUMMARY OF THE INVENTION

The present invention involves the use of synthetic polymeric granules or beads to separate B and T lymphocytes from suspensions of a mixture of B and T lymphocytes. The beads or granules are enclosed in a suitable container such as a cylinder, and the suspension of B and T lymphocytes is passed over the beads or granules. The B-lymphocytes adhere to the beads or granules selectively. After the suspension of B and T lymphocytes has been passed over the beads or granules the B lymphocytes are removed from the beads or granules with a suitable solution.

Suitable beads or granules can be prepared from polyamides, polyurethanes, polyureas, polyesters, polyacrylonitrile, polymethyl methacrylate, polyureaurethanes, polyacrylates and polyolefins. Generally the bead or granule will be formed of a single polymer but blends or coated beads or granules can be used. Various shaped granules can be used but particularly preferred are granules that have smooth surfaces and are spherical or cylindrical in shape. The largest dimension or diameter of the granules should be less than 5 mm (5000 $\mu$m) and preferably is between 200 and 400 $\mu$m.

The B and T lymphocytes can be obtained from mammalian blood, as well as from the spleen, bone marrow, thymus and lymph tissues.

DETAILED DESCRIPTION

Blood is commonly treated with an anticoagulant and centrifuged to effect separation of the various components. The red cells form a lower layer upon which the white blood cells form a layer known as the buffy coat. The supernatant plasma is the pale yellow fluid portion of the blood in which the formed elements (red blood cells, leukocytes and platelets) are suspended. Plasma differs from blood serum in that plasma contains fibrinogen, which is absent once clotting occurs. Clotting leaves blood serum as the remaining fluid. The platelets (thrombocytes), separable by centrifugation, are fragile formed elements which are important in clotting.

Leukocyte is a general term for a white blood cell formed in the myelopoietic, lymphoid and reticular portions of the reticuloendothelial system in various parts of the body. Leukocytes are normally present at those sites and circulating throughout the body. The reticuloendothelial system is the collective name given to the system of cells in different organs which are concerned with phagocytosis or the ability of cells to ingest other cells and particulate matter. The myelopoietic portion refers to the bone marrow, the lymphoid portion to the lymph system, and the reticular portion to the fine network formed by cells in various organs such as in the lymph nodes, liver, spleen and thymus.

Leukocytes are subdivided into several major types which can be distinguished by size and staining techniques. The monocytes are relatively large mononuclear phagocytic leukocytes (16 to 22 $\mu$m in diameter, 0.2 to $1.0 \times 10^6$/ml) which contain numerous small vacuoles and granules. With Wright's stain (eosin and methylene blue) monocytes exhibit a pale blue or blue-gray cytoplasm and numerous fine red and blue granules. The monocyte matures into the macrophage, a cell which synthesizes some of the components of complement and is necessary for initiating both humoral and cellular immune responses. The polymorphonuclear leukocytes have multilobate nuclei and are phagocytic scavenger cells. They are classified into neutrophils (N, $2-7 \times 10^6$/ml, cytoplasmic granules readily stained by neutral dyes), eosinophils (E, $0-0.7 \times 10^6$/ml, cytoplasmic granules are coarse, round and pink to bright red after staining with Wright's stain), and basophils (B, $0-0.15 \times 10^6$/ml, deep purple cytoplasmic granules with Wright's stain). The lymphocytes are mononuclear cells (usually 10 $\mu$m in diameter with some larger ones up to 20 $\mu$m, $1.3-7 \times 10^6$/ml, whose nucleus stains bright purple with a few bright red-violet cytoplasmic granules with Wright's stain) with scant cytoplasma which are involved in immune responses such as antibody production, delayed-type hypersensitivity, inflammation, rejection of tissue or organ transplants and reactions against neoplastic cells.

Lymphocytes, once thought to be a homogeneous population of cells, are now subdivided into B and T lymphocytes, depending upon their history. The B lymphocytes originate in bone marrow and produce, secrete and carry immunoglobulin on their surfaces and are responsible for humoral immunity. The T lymphocytes are lymphocytes originating from the bone marrow but which have been modified by the thymus and are involved mainly in the cell-mediated immune response; they do not readily exhibit immunoglobulins on the cell surface. An immature T lymphocyte isolated from the thymus is called a thymocyte.

Immune responsiveness is the end result of numerous cell-cell interactions. In order for an immune resonse to be induced, the foreign antigen, be it a bacterium, virus, parasite or "altered-self" antigen, must first be processed by a certain subpopulation of macrophages and information presented to uncommitted lymphocytes. These lymphocytes then become "committed" or sensitized and respond in various ways depending upon the nature of the sensitizing antigen, the way it was presented to the macrophage, and the origin of the responding lymphocyte. Thus, a lymphocyte of bone marrow origin (B lymphocyte) might respond by producing antibody of a specific type (e.g., IgM, IgG, IgE, IgA) and a T lymphocyte which is thymus-derived might respond by producing lymphokines (e.g., migration inhibition factor, interferon, lymphotoxin) or become a "killer" cell capable of destroying upon contact the parasite or cell to which it has been sensitized.

The type of immune response and the degree to which the lymphocytes respond is controlled by various B and T lymphocyte subpopulations (e.g., helper, suppressor, amplifier cells). Under- or over-production of any of these cells upsets a delicate balance and the result is an immunopathy such as hypo- or agammaglobulinemia, autoimmunity, tolerance, macroglobulinemia, hypersensitivity, allergy, tumor development or leukemia, or failure to respond to viral, bacterial or fungal infections. Because of the different biological functions of B and T lymphocytes, it is of interest not only from an investigative viewpoint, but also as a potentially useful medical technique to be able to separate these two cell populations.

Techniques used to separate T lymphocytes from B lymphocytes include: (1) the adsorption of B lymphocytes to antigen-antibody complexes, such as hemolysin-coated sheep red blood cells followed by differential centrifugation to remove the complexes, (2) the use of columns of glass or Sepharose beads coated with antibody specific for B or T lymphocytes, (3) the specific lysis of B lymphocytes in the presence of antibody and complement, (4) the use of the fluorescence-activated cell sorter and (5) the adsorption of B lymphocytes to nylon fibers. Of these techniques, the use of nylon fibers is simple, radid, gives relatively pure preparations of viable T lymphocytes, does not involve the use of costly equipment or specific antisera, and B cells can be recovered from the column intact.

The separation of lymphocytes from other nucleated blood elements was described in U.S. Pat. No. 3,462,361 and in T. J. Greenwalt, Gajewski and J. L. McKenna, *Transfusion*, 2, 221 (1962), using a column packed with poly(hexamethylene adipamide) fiber, 3-denier, 1.5-inch staple. Later M. F. Greaves and G. Brown, *J. Immunology*, 112, 420; S. A. Eisen, H. J. Wedner and C. W. Parker, *Immunological Communications*, 1, (6), 571 (1972); B. S. Handwerger and R. H. Schwartz, *Federation Proceedings*, 33, 731 (1974); D. Trizio and G. Cudkowicz, *J. Immunology*, 113, 1093 (1974); and M. H. Julius, E. Simpson and L. A. Herzenberg, *European J. Immunology*, 3, 645 (1973) describe using such polyamide fiber packed columns for the separation of B and T lymphocytes, the B lymphocytes being retained more firmly by the column material than the T lymphocytes which collected in the effluent. The B lymphocytes could subsequently be released from the column material by mechanical agitation or by the use of reagents such as ethylenediaminetetraacetic acid (EDTA).

The main drawback to the use of polyamide fiber-packed columns is the poor recovery; generally less than 60% of the added T lymphocytes are retrievable. This poor recovery represents a serious problem in the study of T lymphocyte subpopulations. Even when the recovered cells are rerun through a second column for further purification, a further 50% of these cells are lost (Greaves et al cited above). The recovery of T lymphocytes is also decreased when the amount of nylon in the columns is increased (Eisen et al cited above). These results suggest that the nylon fibers mechanically trap a considerable portion of the T lymphocytes in their passage through the column.

In the present invention, we have found that the substitution of polymer granules of the types specified herein for nylon fiber produces a dramatic increase in T lymphocyte recovery from about 60% in favorable experiments with the fibers to about 90–100% for the granules. A further advantage of our invention from use of fibers is that fibers contain additives or coatings for textile uses which adversely affect blood cells and their adherence. Granules possess the following advantages when used in the process of separating cellular components:

(1) Granules give excellent control of packing uniformity, resulting in less mechanical trapping of unadsorbed cells.
(2) The absence of channeling in uniformly packed granule columns permits high flow rates through the columns and fast, clean separations of T lymphocytes.
(3) The absence of channeling also permits large colums and hence large volumes of blood or cell suspensions to be used in granule-packed columns.
(4) Commercial nylon fibers contain spin finishes which not only inhibit adherence of cells to the polymer but they or their derived products, e.g. by oxidation, are known to be cytotoxic, as illustrated by the very low recoveries of viable cells from such commercially available column materials. The finish may also produce pyrogenic reactions in the recipient of the blood or blood product samples processed through such columns, and it is necessary to remove these spin finishes from the fiber surfaces. However, this is not done readily with uniform success because of the aging phenomenon, even though careful and time-consuming procedures for doing so have been described, as witnessed by the variable results obtained for the recovery of T lymphocytes in the references cited. The use of a column material free of finish residues eliminates one source of pyrogenic response in the recipient.

Lymphocyte transfusion is useful in providing the recipient cells capable of responding to antigenic challenge by the production of antibodies. Transfusion of B and T lymphocytes, separated by the process of this invention, could be used to restore equilibrium to the immune system of a recipient in whom this system is disturbed, or it could be used to confer cell-mediated immunity to such a patient by means of a purified T lymphocyte transfusion.

Suitable column materials for forming the beads should have the following desirable properties.
(1) Be able to adhere cell types in biological fluids of medical interest.
(2) Be in granular form for reproducible packing into suitable containers.
(3) Have a softening point above 120° C., or even higher, if sterilization by autoclaving is part of the process. Gumminess and distortion after packing would be unacceptable side effects.
(4) Be insoluble in water and aqueous biological media.
(5) Have no leachable cytotoxic materials.

Generally nylon and the polyesters are the preferred materials for forming the beads.

Polymers useful for granules and the preferred beads or spheres whose surfaces are smooth, i.e., free of angular imperfections and cracks or do not have portions that have a very short radius of curvature, preferably are linear high molecular weight organic polymers that melt above 100° and have a relatively low fluid viscosity when in the molten state. Such readily form smooth surface beads which are a preferred form when individual particles of polymers such as short lengths of fibers are heated above the melting point of the polymer in an inert atmosphere and cooled before contacting each other or a hot surface, such as in a shot tower.

Useful thermoplastic polymers include those formed by addition polymerization and copolymerization of olefins, e.g., ethylene, propylene; vinyl halides such as vinyl chloride, vinyl fluoride, vinylidene chloride, vinylidene fluoride, chlorotrifluoroethylene; specific copolymers, e.g., of ethylene with vinyl acetate and/or with carbon monoxide; acrylonitrile; styrene polymers and copolymers are useful. Methyl methacrylate and ether-containing polymers preferentially absorb granulocytes to lymphocytes and are not useful for the present process.

Especially useful are polyamides or polyesters having aliphatic or aromatic groups. These include those formed from the reaction of (a) aliphatic diamines of from 4 to 12 carbon atoms with aliphatic diacids of from 4 to 12 carbons, (b) from aliphatic cyclic lactams of from 5 to 12 carbon atoms, (c) from the reaction of piperazine or N,N'-dialkyl substituted aliphatic diamines of from 4 to 12 carbon atoms with aliphatic diacids of from 4 to 12 carbon atoms, (d) from the reaction of aliphatic diamines of from 4 to 12 carbon atoms with aromatic acids such as isophthalic or tetraphthalic; and (e) copolyamides formed from the reaction of two or more diamines with one diacid or from two or more diacids with one diamine.

Especially preferred are those polyamides known as nylon 6 (polyhexaneamide), nylon 66 [poly(hexamethylene adipamide)], nylon 610 [poly(hexamethylene decaneamide)], nylon 612 [poly(hexamethylene dodecaneamide)], nylon 11 (polyundecaneamide), nylon 12 (polydodecaneamide), and those copolyamides known as nylon 66+610 [poly(hexamethylene adipamide+decaneamide)] and nylon (6+66+610) [poly(hexaneamide+hexamethylene adipamide+decaneamide)].

Also preferred are the polyesters formed by the reaction of an aliphatic diol from 2 to 10 carbon atoms with terephthalic, isophthalic or phthalic acids, for example, poly(ethylene terephthalate), poly(butylene terephthalate) and poly(1,4-cyclohexanedimethylene terephthalate); poly[4-(2-hydroxyethyl)benzoic acid] and copolymers of ethylene glycol or polyethylene glycol with terephthalic and isophthalic, 4-hydroxybenzoic or 1,2-diphenoxyethane-4,4'-dicarboxylic acids.

Also suitable are polyurethanes derived from the reaction of aliphatic diols from 2 to 10 carbon atoms with aliphatic diisocyanates of from 2 to 10 carbon atoms, or 4,4'-tolylene diisocyanate, or 4,4'-diphenylmethane diisocyanate, or 1,5-(naphthylene diisocyanate); copolymers or capped forms of poly(ethylene adipate), poly(ethylene sebacate), poly(diethylene glycol adipate), poly(ethylene sebacate), poly(diethylene glycol adipate), poly(oxytetramethylene glycol) or trimethylolpropanepropylene oxide copolymer with the above diisocyanates. Polyureas derived from the reaction of aliphatic diamines of from 2 to 10 carbon atoms with the above diisocyanates can be used.

Cellulose esters, for example, cellulose acetate-butyrate can be used for preparation of granules and even spheres.

Smooth surface spheres are formed from (1) cylinders of desired length cut from fibers; (2) powders of desired sieve size obtained by cryogenically grinding flake or commercial molding pellets and dropping the particles of polymer through a hot zone of inert gas such as helium, argon, or nitrogen. The temperature required will depend on the melting temperature of the particle, the size of the particle, and the length of the heated zone in the "shot tower". A large particle takes longer to melt through than a small particle. This may require increasing the temperature of the heating zone, and/or the length of the heating zone to provide more time for melting. For particles preferred for blood cell separation, temperatures are from about 200° C. to 950° C. Nylon and polyester sherical beads were generally made with shot tower temperatures of about 300°–375° C. Quenching is readily accomplished with nylon and polyester by having the tower extend 2 to 3 feet or more below the furnace to allow the particles to solidify before they are collected at the bottom of the tower. To facilitate quenching, the inert gas used in the column is fed into the bottom of the tower and out the top of the tower.

Inorganic substances such as glass are undesirable for forming the beads for a variety of reasons. The handling of glass and other inorganic beads creates a problem because such substances generally are brittle and tend to fracture on handling. The small fragments thus produced can pass through the foraminous support for the bed of beads and become part of the leukocyte lean blood which is highly undesirable.

Spheres may be formed from fibers of the above polymers of any desired diameter from 0.005 mm to 5 mm in diameter by extrusion without additives, and collection without orientation (free-fall) or with orientation (under tension) with any desired cross-sectional shape such as circular, elliptical, rectangular, square, trilobal, keyhole or cruciform cross-section. These fibers may then be chopped into lengths of usually 0.1 to 5 mm with the preferred diameter being between 0.2 mm and 0.4 mm. Other ways of achieving granular polymers are to cryogenically grind any of the above forms of the above polymers and separate the different sized particles by sieving, and to quench droplets of molten polymer to form particles of a desired size. Granules of 20 to 60 mesh size (0.062–0.8 mm) are particularly effective in this application.

The pH of the medium in which lymphocytes are handled should not vary significantly from that of physiologic conditions, i.e., pH 6.9 to 7.5. The best recovery of T lymphocytes is found when the eluting medium is kept at pH 7.

The flow rate of the medium through a gram of the granules in a column should be between 3–5 ml/min for separating B and T lymphocytes. Flow rates below 3 ml/min/g of granules reduce the T lymphocyte recovery, while flow rates above 5 ml/min/g of granules cause increased contamination of T lymphocytes with B lymphocytes.

The presence of serum in the elution medium and during cell handling and incubation greatly aids the recovery of the T lymphocytes. Between 3 and 8% serum is useful in this respect, and preferably 5% serum is used for maximum recovery of T lymphocytes.

More complete recovery of adherent cells results from increasing the volume of the assembly containing polymer particles (including granules, spheres, rods) when treated with eluant. This can be accomplished by use of an exandable, e.g., accordion type, flexible container during the elution suitably by backwashing, whereby the volume of combined eluant and polymer particles is greater by at least 25% and generally 50–600% than the volume of the particles and cell suspension contacting them at any one time.

Good recoveries of T lymphocytes can be made between 4° C. and 25° C.; for convenience, it is preferable to use room temperature (20°–25° C.). Little attachment to polymer granules takes place below 4°.

EXAMPLES

Procedures A to E below describe how the cell materials were prepared, separated and identified in the Examples.

Procedure A

Preparation of Spleen Cell Suspensions

Spleens were removed aseptically from etherized mice ($C_3H$/HEJ stain) or rats (Lewis) and placed in RPMI-1640 medium (Grand Island Biological Company) supplemented with glutamine (2 mM/ml) and gentamicin (Schering Corp. 50 $\mu$g/ml). The spleen cells were teased from the connective tissue by forcing the tissue through a fine mesh steel screen. After allowing the coarse material to settle, cells contained in the supernatant fluid were washed once with cold medium, pelleted by centrifugation and then suspended in approximately 8 volumes of ice cold 0.83% $NH_4Cl$, pH 7.0 in order to lyse red blood cells present in the suspension. After several minutes at 4° C. the cells were washed three times more and then suspended in serum free RPMI-1640 medium. A viable cell count was done using erythrocin B and a hemocytometer and the cell concentration was adjusted to contain the desired number of viable cells/ml.

Procedure B

Preparation of Thymus Cells

Thymus cells were prepared according to the technique described for the preparation of spleen cells. The enzyme DNase (Worthington Biochemical), 1,000–5,000 $\mu$g, was present in the medium during the separation of the cells from thymus connective tissue to prevent trapping of individual cells in viscid DNA released from damaged thymocytes.

Procedure C

Preparation of Human Peripheral Leukocytes

Blood taken from human volunteers by venipuncture was mixed with heparin (200 units/10 ml blood) and dextran (avg. mol. wt. 240,000; 2 ml of a 5% solution dextran/10 ml blood) and then placed at 37° for 30 minutes to allow the red blood cells to settle. The leukocyte-rich plasma was collected and mixed with phosphate buffered saline (PBS), pH 7.2, and centrifuged for 10 min. at 300×g. The leukocytes were washed once with PBS, suspended in Eagle's minimum essential medium (MEM, Grand Island Biological Co.) supplemented with 7% fetal calf serum (fcs, Grand Island Biological Co.), and counted using a hemocytometer. An aliquot of the cell suspension was stained in order to determine the percent mononuclear cells present in the suspension. The cells were diluted with MEM+7% fcs to the desired cell concentration.

Procedure D

Preparation of Lymphocytes

Occasionally, it was desirable to have lymphocytes devoid of phagocytic polymorphonuclear leukocytes and monocytes. Leukocytes obtained from either human peripheral venous blood or mouse spleen or thymus were suspended in medium at a concentration of $10 \times 10^6$ cells/ml and placed in 32 oz. Falcon plastic flasks or 60×15 mm dishes (specially treated to cause phagocytic cells to stick to them). Phagocytic cells were allowed to attach to the culture vessel surface overnight at 37° and the nonadhering lymphocytes were recovered in the medium the next day. This procedure results in cell suspensions that are greater than 80% lymphocytes.

Procedure E

Column Procedure for the Separation of B and T Lymphocytes

Synthetic fibers or pellets were treated overnight with 0.1 N HCl, washed extensively with distilled water, dried and then placed in 12 ml Monoject ® (Sherwood Medical Industries) disposable syringes, with approximately 1 g of fiber or 6 g of pelleted (2.5 mm×2.5 mm) nylon per syringe. The packed syringes were sterilized in a steam autoclave for 15 min and stored at room temperature until needed. Before using the syringes to separate B and T lymphocytes, the columns were rinsed with approximately 25 ml of RPMI-1640 medium containing 5% fcs with the column packing being completely covered by the medium. The columns were drained and 6–8 ml of medium was added to each column. The columns were then placed at 37° C. for 1 hour, after which the columns were again drained. One column volume of medium containing $1-10\times10^7$ cells (preferably lymphocytes) was added to each column and the columns were returned to the incubator for an additional 30–45 min. Non-adherent T lymphocytes were recovered by allowing 50 ml of medium to flow through the column at a rate of approximately 3–5 ml/min. B Lymphocytes were recovered by agitating the fiber in the presence of medium and then removing the medium which contains the detached lymphocytes.

Three procedures have been used to fix the cells to slide for evaluation.
  a. Cell-spreading—Acid cleaned microscope slides are flooded with a fixative consisting of 1 part glacial acetic acid and 3 parts absolute ethyl alcohol. The slides are drained and a drop of cell suspension (approximately $5\times10^4$ cells) placed on each slide. The slides are washed using the fixative and allowed to air dry.
  b. Approximately $1\times10^5$ cells in 0.1 to 0.2 ml are placed in the wells of a Shandon Cytocentrifuge. The cells are allowed to centrifuge down on to glass slides for 3 min at 1,500 rpm. The slides are then dipped in 70% ethyl alcohol and allowed to air dry.
  c. The same technique for fixing the cells to slides using the Shandon Cytocentrifuge is used; however, the cells are first reacted with fluorescein-labeled antibody and washed several times with PBS efore fixing.

Several fluorescent staining techniques have been used to determine the percent B and T lymphocytes present in a cell preparation.
  a. Cells are reacted for 20 min at 37° C. with rabbit antithymocyte serum, washed and then stained with fluorescein-labeled goat anti-rabbit serum. The T lymphocytes fluoresce.
  b. Cells are reacted with AKR anti-$C_3H$ theta serum followed by staining the T lymphocytes with fluorescein-labeled rabbit anti-mouse immunoglobulin antibody for 20 min at 37° C.
  c. B Lymphocytes are stained directly with fluorescein-labeled antibody prepared against immunoglobulins from the species under study, i.e., mouse, rat, human. Cell immunofluorescence is determined at a magnification of 640× using a Zeiss fluorescent microscope equipped with a dark field condenser APO 40× oil immersion objective and BG-12 exciter and 50 barrier filters to observe fluorescence. The specificity of the immune fluorescent staining reactions are determined by using nonimmune sera or by blocking fluorescence using immune sera without fluorescein.

An alternative and preferred method which involves no fixing is referred to as the "wet mount". Lymphocytes in suspension are stained directly with fluorescein-labeled antibody prepared against the appropriate immunoglobulins. These preparations are incubated at 37° C. for 20 to 30 min, washed free of unadsorbed fluoresceinated antibody, and a drop containing cells is counted directly without further fixing. The number of lymphocytes in the starting and eluted cell suspensions were counted by Cytograph Model 6302 (Bio/Physics Systems, Mahopac, N.Y., division of Ortho Instruments of Westwood, Mass.).

EXAMPLE 1

T Lymphocyte Separation from Mouse Spleen Using Polyhexamethylene Adipamide Granules and Fibers Columns were prepared as described in Procedure E above from (a) polyhexamethylene adipamide oriented fiber, 1.5-inch staple, 3.0 denier, and (b) polyhexamethylene adipamide granules, 2.5 mm molding granules.

Mouse spleen cell suspensions prepared as described in Procedures A and D were separated on these columns by the procedure of Procedure E. The results given in Table I clearly show that the recovery of T lymphocytes from columns packed with granules is far superior to that recovered from columns packed with fiber without affecting the purity of the eluted cell suspensions.

TABLE I

| Material | % T Cell Recovery | | Purity (% T Cells in Eluate) | |
|---|---|---|---|---|
| | Exp 1 | Exp 2 | Exp 1 | Exp 2 |
| Granules | 89 | 96 | 80 | 83 |
| Fiber | 57 | 64 | 75 | 77 |

EXAMPLE 2

T Lymphocyte Separation from Mouse Spleen Using Different Sized Granules of Polyhexamethylene Adipamide Polyhexamethylene adipamide granules of various sizes were prepared from ground extrusion resin, by sieving. Columns of these sieved materials were prepared and used as described in Procedure E with cell suspensions prepared from mouse spleen as in Procedures A and D. The results given in Table II show that the efficiency of T lymphocyte recovery is unaffected by reduction of the granule size to −20+60 mesh (U.S. Sieve). Accuracy of the count is about ±15%.

TABLE II

| Size of Granules | % T Cell Recovery | Purity (% T Cell in Eluate) |
|---|---|---|
| 2.5 mm | 93 | 91 |
| + 20 mesh | 116 | 85 |
| −20 + 60 mesh | 104 | 100 |

EXAMPLE 3

T Lymphocyte Separation from Mouse Spleen and Thymus Using Polyhexamethylene Adipamide and Polyhexamethylene Dodecanamide Columns of (a) polyhexamethylene adipamide, 2.5 mm molding granules and (b) polyhexamethylene dodecanamide, 2.5 mm molding granules were prepared and used as described in Procedure E.

Cell preparations from mouse spleen (Procedures A and D) and mouse thymus (Procedures B and D) were passed down these columns as described in Procedure E. The results given in Table III show that polyhexamethylene dodecaneamide (nylon 612) granules are as effective as polyhexamethylene adipamide (nylon 66) granules in separating T lymphocytes from the two sources.

TABLE III

| Nylon Type | % T Cells Recovered* | | | Purity (% T Cells in Eluate) | | |
|---|---|---|---|---|---|---|
| | Exp 1 Spleen | Exp 2 Thymus | Exp 3 Thymus | Exp 1 Spleen | Exp 2 Thymus | Exp 3 Thymus |
| 66 | 100 | 100 | 100 | 85 | 100 | 100 |
| 612 | 97 | 99 | 102 | 89 | 100 | 100 |

*The recovery of T cells from columns of nylon 66 was set at 100% to facilitate comparison of recoveries from nylon 612 columns.

EXAMPLE 4

T Lymphocyte Separation from Mouse Spleen Using Fibers of Different Filament Size Columns of polyhexamethylene adipamide fiber cylinders of 38 mm length were prepared and used as described in Procedure E with mouse spleen cell preparations obtained as in Procedures A and D. In Table IV, entry 1 is polyhexamethylene adipamide, 2.5 mm molding granules; entries 2A–2F were prepared by spinning bulk polyhexamethylene adipamide (free of additives and surface finishes) at a temperature of 270°–288° C. with the spinnerette size and pressure indicated; entries 2A–2E were unoriented "free fall" fibers collected in a battery jar; entry 2F was an oriented fiber obtained by winding the monofilament onto spools at 600 ft/min; entry 3 was commercial polyhexamethylene adipamide, 38 mm staple, 3.0 denier treated to remove spin finish as in Procedure E. The monofilaments in entries 2A–2F were chopped into lengths of approximately 38 mm before being packed in the column. The results given in Table IV show that generally, the smaller the fiber diameter, the less efficient was the material in regard to recovery of T Lymphocytes from the column. There was also a significant day-to-day variation with the finer fibers, suggesting that recovery of T lymphocytes from the fibers was decreased by mechanical trapping of the cells in the wet fiber mesh, which, in turn, was influenced by the degree of compaction of the fibers in the columns.

TABLE IV

Comparison of Nylon 66 Granules with Nylon 66 Experimental Fibers (A) Filament Diameter and Orientation

| Materials | | Filament Diameter (mm) |
|---|---|---|
| (1) | Nylon 66 Granules | 2.5 |
| (2) | Nylon 66 Fibers | |

TABLE IV-continued
Comparison of Nylon 66 Granules with Nylon 66 Experimental Fibers

| | | |
|---|---|---|
| | A | 1.26–2.43 |
| | B | 0.97–1.39 |
| | C | 0.85–0.93 |
| | D | 0.47–0.53 |
| | E | 0.12–0.15 |
| | F+ | 0.02–0.03 |
| | | (6 denier) |
| (3)+ | Nylon 66 Fiber (commercial) | 0.01–0.02 (3 denier) |

+Oriented fibers; the other fibers and granules are unoriented.

(B) Cell Recovery

| | | % T Cell Recovery | | | Purity (% T Cells in Eluate) | | |
|---|---|---|---|---|---|---|---|
| | Materials | Exp 1 | Exp 2 | Exp 3 | Exp 1 | Exp 2 | Exp 3 |
| (1) | Nylon 66* Granules | 100 | 100 | 100 | 85 | 85 | 85 |
| (2) | Nylon 66 Fibers | | | | | | |
| | A | 105 | | | 82 | | |
| | B | 82 | | | 82 | | |
| | C | 73 | | | 67 | | |
| | D | 83 | 71 | | 78 | 84 | |
| | E | 73 | 41 | | 84 | 85 | |
| | F+ | 75 | 42 | 56 | 72 | 91 | 90 |
| (3)+ | Nylon 66 Fiber (commercial) | 64 | 67 | | 75 | 77 | |

*The percent recovery of T cells from columns was set at 100% to facilitate comparison with the percent recoveries of cells from various nylon fibers versus granules.

EXAMPLE 5

T Lymphocyte Separation from Mouse Spleen Using Mixed Copolyamides

Columns of polyhexamethylene adipamide, 2.5 mm molding granules, and mixed copolyamides A, B and C shown below, as molding flake, were prepared and used as described in Procedure E with cells prepared from mouse spleen as described in Procedures A and D. The results in Table V show that samples B and C are as effective as granular polyhexamethylene adipamide in separating T lymphocytes.

Sample A has the segmental structures:

—HN(CH$_2$)$_6$NH—CO(CH$_2$)$_4$CO—    70 wt %

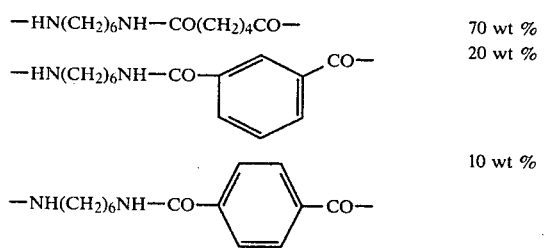

20 wt %

10 wt %

Sample B has the segmental structures:

  90 wt %

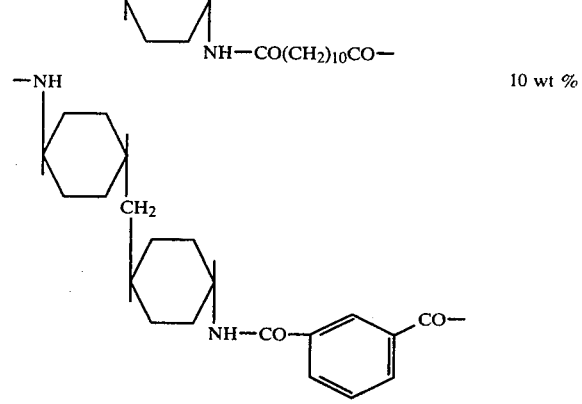  10 wt %

Sample C has the segmental structures:

—HN(CH$_2$)$_6$NH—CO(CH$_2$)$_4$—CO—    98 wt %

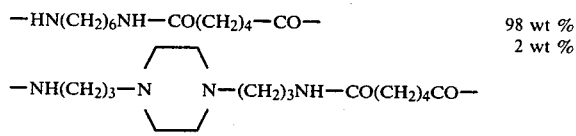  2 wt %

TABLE V
Comparison of Nylon 66 with Mixed Copolyamides

| Material | Physical Form | % T Cells Recovered | Purity (% T Cells in Eluate) |
|---|---|---|---|
| Nylon 66 | 2.5 mm granule | (a) 115 (b) 120 | 73 |
| A | Flake | (a) 72 (b) 80 | 72 |
| B | Flake | (a) 98 (b) 110 | 81 |
| C | Flake | (a) 137 (b) 124 | 86 |

(a) First experiment     (b) Second experiment

EXAMPLE 6

T Lymphocyte Separation from Human Peripheral Blood Using Nylon 66 Granules

Human peripheral blood prepared as described in Procedure C above was allowed to stand twice at 37° C. for 0.5 hr. in plastic dishes as described in Procedure D in order to remove phagocytic cells. The lymphocyte suspension was passed down a column of polyhexamethylene adipamide, 2.5 mm molding granules as described in Procedure E. This procedure gave an 88% recovery of T cells of 87% purity (% T cells in eluate).

EXAMPLE 7

T Lymphocyte Separation from Rat Spleen and Thymus Using Nylon 66 Granules

Rat spleen and thymus preparations were made following Procedures A, B and D, and passed down columns of polyhexamethylene adipamide, 2.5 mm molding granules as described in Procedure E. The results given in Table VI show that these columns efficiently separated T lymphocytes of rat origin.

TABLE VI

Separation of T Lymphocytes of Rat Origin

| Material | % T Cells Recovered | Purity (% T Cells in Eluate) |
|---|---|---|
| Rat Spleen | 97 | 85 |
| Rat Thymus | 90 | 100 |

EXAMPLE 8

Separation of T Lymphocytes by Multiple Passage Through Nylon 66 Granule Columns Two columns of polyhexamethylene adipamide 2.5 mm molding granules were prepared and used serially as described in Procedure E with cells prepared from mouse spleen as described in Procedures A and D. The cells recovered from the first column were separated by centrifugation of the eluate, and resuspended in 5 ml of medium for passage down the second column. This effected a further purification of the T lymphocytes as shown in Table VII.

TABLE VII

Multiple Passage Purification of T Lymphocytes

| Passage No. | % T Cells Recovered | Purity (% T Cells in Eluate) |
|---|---|---|
| 1 | 78 | 74 |
| 2 | 100 | 90 |

EXAMPLE 9

Effect of Temperature on Recovery of T Lymphocytes From Nylon 66 Granule Columns Three columns of polyhexamethylene adipamide, 2.5 mm molding granules were prepared and used as described in Procedure E with cells prepared from mouse spleen as described in Procedure A and D. The columns were equilibrated to either 6° C., 23° C. or 37° C. before use and all media, glassware and cell suspensions were maintained at these respective temperatures for the duration of the experiment. The results in Table VIII indicate that temperatures in the range of 6°-23° C. gave better recoveries than at 37° C.

TABLE VIII

Effect of Temperature on Recovery of T Lymphocytes

| Temperature (°C.) | % T Cell Recovery |
|---|---|
| 6 | 67 |
| 23 | 68 |
| 37 | 49 |

EXAMPLE 10

Effect of Serum on Recovery of T Lymphocytes From Nylon 66 Granule Columns

The presence of fetal calf serum in the elution medium was studied by using six columns of polyhexamethylene adipamide, 2.5 mm molding granules, prepared and used as described in Procedure E with cells prepared from mouse spleen as described in Procedures A and D. The results in Table IX show that maximum recovery of T lymphocytes occurred when 5% fetal calf serum was included in the medium and that the presence of 1 to 10% fetal calf serum greatly enhances the recovery of T leukocytes.

TABLE IX

Effect of Serum on Recovery of T Lymphocytes From Nylon 66 Granules

| Medium | Serum (%) | Recovery of T Cells (%) |
|---|---|---|
| PBS | 0 | 33 |
| RPMI-1640 | 0 | 43 |
| RPMI-1640 | 0.1 | 49 |
| RPMI-1640 | 1 | 71 |
| RPMI-1640 | 5 | 83 |
| RPMI-1640 | 10 | 82 |

We claim:

1. A process comprising passing an aqueous suspension of a mixture of B lymphocytes and T lymphocytes through a bed of synthetic polymeric granules having a diameter of from 0.1 to 5 mm at a temperature of from about 4° C. to about 25° C. whereby the B lymphocytes become adhered to the granules and the T lymphocytes pass through the bed.

2. The process of claim 1 wherein the pH of the suspension is from 6.9 to 7.5.

3. The process of claim 2 wherein the suspension contains from 1 to 10 percent serum.

4. The process of claim 3 wherein the granules are made of a synthetic polymer selected from the class consisting of polyamides and polyesters.

5. The process of claim 4 wherein the synthetic polymer is a polyamide.

6. The process of claim 5 wherein the polyamide is polyhexamethylene adipamide.

7. The process of claim 4 wherein the synthetic polymer is a polyester.

* * * * *